US006673608B1

United States Patent
Deyu et al.

(10) Patent No.: US 6,673,608 B1
(45) Date of Patent: Jan. 6, 2004

(54) SOMATIC EMBRYOGENIC REGENERATION OF *ACACIA MANGIUM*

(75) Inventors: Xie Deyu, Singapore (SG); Hong Yan, Singapore (SG)

(73) Assignee: Institute of Molecular Agrobiology (SG)

( * ) Notice: Subject to any disclaimer, the term of this patent is extended or adjusted under 35 U.S.C. 154(b) by 0 days.

(21) Appl. No.: 10/069,043

(22) PCT Filed: Jun. 21, 2000

(86) PCT No.: PCT/SG00/00110

§ 371 (c)(1), (2), (4) Date: Jul. 24, 2002

(87) PCT Pub. No.: WO01/97600

PCT Pub. Date: Dec. 27, 2001

(51) Int. Cl.$^7$ .............................. C12N 5/00; C12N 5/02
(52) U.S. Cl. .................................... 435/430.1
(58) Field of Search ...................... 435/430.1

(56) References Cited

FOREIGN PATENT DOCUMENTS

WO          WO 97/23126 A2      7/1997

OTHER PUBLICATIONS

D.Y. Xie et al., "Regeneration of *Acacia mangium* through somatic embryogenesis," *Plant Cell Reports* 20:34–40, 2001.

C.A. Huetteman et al., "Thidiazuron: a potent cytokinin for woody plant tissue culture," *Plant Cell, Tissue and Organ Culture* 33:105–119, 1993.

B.N.S. Murthy et al., "Thidiazuron: A Potent Regulator of In Vitro Plant Morphogenesis," *In Vitro Cell. Dev. Biol.* —*Plant* 34:267–275, Oct.–Dec. 1998.

P. Lakshmanan et al., "Somatic Embryogenesis in Leguminous Plants," *Plant Biol.* 2:136–148, 2000.

G. R. Rout et al, "Somatic embryogenesis and plant regeneration from callus culture of *Acacia catechu*—a multipurpose leguminous tree," *Plant Cell, Tissue and Organ Culture* 42:283–285, 1995.

*Primary Examiner*—Bruce R. Campbell
*Assistant Examiner*—Susan B. McCormick
(74) *Attorney, Agent, or Firm*—Rothwell, Figg, Ernst & Manbeck, pc (57) ABSTRACT

The present invention relates to the field of somatic embryo production, particularly to methods for the regeneration of *Acacia mangium* through somatic embryogenesis. More specifically, the present invention relates to a method for regeneration of plants of *Acacia mangium* by culturing explants of immature zygotic embryos on callus induction medium to grow embryogenic tissue. Culturing of the embryogenic tissue is continued on somatic embryo maturation medium and germination medium. The germinated embryos are further converted to acclimatized plants for field planting. The method is well suited for producing clonal planting stock useful for reforestation.

21 Claims, 4 Drawing Sheets

SOMATIC EMBRYOGENIC REGENERATION OF *ACACIA MANGIUM*

BACKGROUND OF THE INVENTION

The present invention relates to the field of somatic embryo production, particularly to methods for the regeneration of *Acacia mangium* through somatic embryogenesis. More specifically, the present invention relates to a method for regeneration of plants of *Acacia mangium* by culturing explants of immature zygotic embryos on callus induction medium to grow embryogenic tissue. Culturing of the embryogenic tissue is continued on somatic embryo maturation medium and germination medium. The germinated embryos are further converted to acclimatized plants for field planting. The method is well suited for producing clonal planting stock useful for reforestation.

The publications and other materials used herein to illuminate the background of the invention or provide additional details respecting the practice, are incorporated by reference, and for convenience are respectively grouped in the appended List of References.

Forests are very important to the world economy and for maintaining and preserving our ecosystem. Forest trees have a wide range of commercial uses (timber for construction, raw material for paper and pulp production, and as an energy source). The global demand for wood products (mostly for paper and pulp and firewood in developing countries) has been increasing year by year when the natural forests are in short supply. Re-forestation is the solution to meeting such increasing demand. Usually, the fast-growing, widely adapted tree species are chosen for re-forestation. Most tree-improvement programs are based on the management of genetic resources, including the selection of superior clones from existing forests, the conservation of genetic variability, partially controlled propagation and classical breeding for desired traits. In spite of the fact that it usually takes several generations to breed, this traditional breeding has been successful in getting elite trees with fast and uniform growth. However, many other traits such as disease and insect resistance, different lignin composition and content are difficult to acquire mainly due to high heterozygosity in tree species and big segregation population. Moreover, the gene(s) conferring certain phenotypes like disease resistance may not be in the gene pool at all. On the other hand, molecular breeding based on genetic transformation of tree species offers the possibility to introduce a particular phenotype without affecting the genetic background of a cultivar. Genetic transformation in Populus species and Eucalyptus species enabled some success in modification of lignin content (Tzfira et al., 1998; Robinson, 1999). The precondition of molecular breeding of forest tree species is the availability of a reliable and reproducible genetic transformation method, which in turn relies on a system of regeneration of one whole plant from a single cell.

Genus Acacia comprises about 1200 tropical and subtropical tree species. It belongs to the family Mimosaceae. *Acacia mangium* is a multipurpose, fast growing and nitrogen fixing elite tropical legume tree. *A. mangium* has been increasingly used for plantation, reforestation and soil rehabilitation in degraded soil. Many *A. mangium* plantations have been established in acidic soil or abandoned land. Yielding high quality fibre, *A. mangium* has been increasingly planted in many regions of South East Asia like Malaysia (Tsai, 1988) and Indonesia as raw material for pulp industry. Many paper and pulp mills in Indonesia have been increasingly relying on plantation as the source of wood and *A. mangium* is the preferred choice. Asia Paper and Pulp group has two affiliate companies with total concession of 540,000 hectares. By 1996, one company had planted 123,000 hectares of *A. mangium*, about 90% of its plantation, which represented 180 million seedlings. It was estimated that by 2004, Asia Paper and Pulp group will virtually source all its wood from plantation, mainly *A. mangium* plantation (Bayliss, 1998a, 1998b). However, the flowers of *A. mangium* show weak protogyny and variable levels of andromonoecy. It possesses the characteristics of self-pollination, cross-intraspecific pollination or interspecific pollination with *A. auriculiformis* in nature (Sedgley et al., 1992; Sornsathapornkul and Owens, 1999). These characteristics of reproduction are disadvantageous to commercial propagation and plantation through seeds.

Regeneration is often used in woody tree propagation (Kozlowski and Pallardy, 1997). In Acacia, a few species were reported the success of regeneration, such as *Acacia catechure* regeneration via somatic embryogenesis (Rout et al., 1995) and *A. auriculiformis* regeneration through organogenesis (Rao and Prasad, 1991). *A. mangium* shoot propagation was reported (Bhaskan and Subbash, 1996; Ahmad, 1991; Galiana et al., 1991a, 1991b;) and Toshihiro (1999) also reported the isolation of protoplast from sterile *A. mangium* seedlings. Our PCT patent application No. PCT/SG00/00010 describes *A. mangium* regeneration through organogenesis. However, regeneration of *A. mangium* through somatic embryogenesis has not been described.

Somatic embryos are clonal in origin and thus multiplication using somatic embryos can have the potential for exceedingly high rates of vegetative increase and is therefore of considerable commercial interest. Regeneration via somatic embryogenesis is an attractive option for plant tissue culture. Somatic embryos reportedly provide more stable regenerants than shoots. Another advantage of regeneration systems using somatic embryos is their apparent single cell origin. This means that it is unlikely that regenerants are of chimerical origin, since, if a regenerant originates from a cluster of cells rather than a single sell, the plant tissues may be chimerical or unstable and produce off-types. The availability of somatic embryogenesis protocols for potato, or other crop species recalcitrant to somatic embryogenesis, will permit these crops to take advantage of any new artificial seed technology advances.

Somatic embryos are suitable for transformation via *Agrobacterium tuniefaciens* (Mathews et al., 1992), microinjection (Neuhaus et al., 1987) and particle bombardment (Wilde et al., 1992). In addition, somatic embryos can be cryopreserved using liquid nitrogen without loss of viability. Cryopreservation is an efficient means of maintaining germplasm and enables plant material to be transported over large distances. Furthermore, somatic embryos are suitable for the development of artificial seed technology (U.S. Pat. No. 5,572,827; Bajaj, 1995a).

Thus, it is an object of the present invention to provide a method for regeneration of *A. mangium* through somatic embryogenesis.

SUMMARY OF THE INVENTION

The present invention relates to the field of somatic embryo production, particularly to methods for the regeneration of *Acacia mangium* through somatic embryogenesis. More specifically, the somatic embryogenesis process for *A. mangium* of the present invention can be divided into four general steps: (1) embryogenic callus induction, (2) embryo maturation, (3) embryo germination, and (4) conversion into acclimatized plants, i.e., regenerated plants or regenerants. The acclimatized plants are then transferred to the field. It is preferred to use a two step embryo maturation.

The present invention also relates to a process for preparing somatic embryos for *A. mangium*. This process generally comprises the first two previously described steps. The somatic embryos can be used as a source material for preparing transgenic plants, can be cryopreserved and can be developed into artificial seed.

According to one embodiment of the present invention, somatic embryogenesis of *Acacia mangium* is achieved from callus induced from immature embryo axes on MS basal medium supplemented with the combinations of thidiazuron (IDZ) and indole-3-acetic acid (IAA) together with ascorbic acid, asparagine, casein enzymatic hydrolysate, glutamine, proline, sucrose and phytagel. Through two steps of maturation procedure by culturing somatic embryos first on ½ MS basal medium containing sucrose, phytagel and gibberellic acid ($GA_3$) and then on ½ basal medium containing sucrose and phytagel, 42.33% of globular embryos developed into torpedo and cotyledon embryos. 11% of mature somatic embryos germinated into seedlings that were transferred to pot soil consisting of a mixture of peat soil and sand.

BRIEF DESCRIPTION OF THE FIGURES

FIGS. 1A–D show somatic embryo induction.

FIGS. 2A–F show somatic embryo maturation and germination. FIG. 2A shows maturation of somatic embryos on AM-425. FIGS. 2B–F show various stages of somatice embryo maturation and germination with FIG. 2B showing torpedo stage, FIG. 2C showing early cotyledon stage, FIG. 2D showing cotyledon stage, FIG. 2E showing somatic embryo germination, and FIG. 2F showing a somatic embryo with single cotyledon.

FIGS. 3A–H show the histology of *A. mangium* somatic embryogenesis. FIGS. 3E–G show globular embryo formation; and, FIG. 3H shows a heart embryo. Abbreviations used are: dc=demarcation cell layer; pe=proembryonic structure; sec=subepidermal cell; sus, suspensor; and, tdc=two-daughter cell.

FIGS. 4A–C show somatic embryo germination.

DETAILED DESCRIPTION OF THE INVENTION

The present invention relates to the field of somatic embryo production, particularly to methods for the regneration of *Acacia mangium* through somatic embryogenesis. More specifically, the present invention relates to a method for regeneration of plants of *Acacia mangium* by culturing explants of immature zygotic embryos on callus induction medium to grow embryogenic tissue. Culturing of the embryogenic tissue is continued on somatic embryo maturation medium and germination medium. The germinated embryos are further converted to acclimatized plants for field planting. The method is well suited for producing clonal planting stock useful for reforestation.

Propagation by somatic embryogenesis refers to methods whereby embryos are produced in vitro from small pieces of plant tissue or individual cells. The embryos are referred to as somatic because they are derived from the somatic (vegetative) tissue, rather than from the sexual process. Vegetative propagation via somatic embryogenesis has the capability to capture all genetic gain of highly desirable genotypes. Furthermore, these methods are readily amenable to automation and mechanization. These qualities endow somatic embryogenesis processes with the potential to produce large numbers of individual clones for reforestation purposes.

In one embodiment of the present invention, somatic embryos are produced by a process which can be divided into two general steps: (1) embryogenic callus induction and (2) embryo maturation. It is preferred to use a two step embryo maturation. In one aspect, somatic embryos are prepared by (a) inducing embryogenic callus on a callus induction medium comprising a basal medium supplemented with TDZ and IAA, (b) maturing the embryos on a first maturation medium comprising a basal medium supplemented with $GA_3$ and (c) maturing the embryos on a second maturation medium comprising a basal medium.

In a second embodiment of the present invention, regenerant plants of *A. mangium* are produced by a process which can be divided into four general steps: (1) embryogenic callus induction, (2) embryo maturation, (3) embryo germination, and (4) conversion into acclimatized plants. It is preferred to use a two step embryo maturation. The acclimatized plants can then be planted in the field. In one aspect, *A. mangium* regenerants are prepared by (a) inducing embryogenic callus on a callus induction medium comprising a basal medium supplemented with TDZ and IAA, (b) maturing the embryos on a first maturation medium comprising a basal medium supplemented with $GA_3$, (c) maturing the embryos on a second maturation medium comprising a basal medium, (d) germinating the mature embryos on germination medium comprising a basal medium and (e) acclimatizing the germinated plants in potting soil.

More specifically with respect to this latter embodiment, somatic embryogenesis of *Acacia mangium* Willd. was achieved from callus induced from immature embryo axes on MS basal medium supplemented with the combinations of TDZ (1–2 mg/l) and IAA (0.25–2 mg/l) together with ascorbic acid (Vc) 100 mg/l, asparagine (Asn) 150 mg/l, casein enzymatic hydrolysate (CH) 100 mg/l, glutamine (Gln) 150 mg/l, proline (Pro) 150 mg/l, sucrose 30 g/l and phytagel 0.3%. Through two steps of maturation procedure by culturing somatic embryos on ½ basal MS medium containing 30–50 g/l sucrose, 0.1% activated charcoal, 0.35% of phytagel and 2.5 mg/l–5.0 mg/l, preferably 5.0 mg/l, of $GA_3$ together with Vc 100 mg/l, Asn 150 mg/l, CH 100 mg/l, Gln 150 mg/l and Pro 150 mg/l, then on ½ basal medium containing 50 g/l of sucrose and 0.35% of phytagel together with Vc 100 mg/l, Asn 150 mg/l, CH 100 mg/l, Gln 150 mg/l, Pro 150 mg/l and 0.1% activated charcoal, 42.33% of globular embryos developed into torpedo and cotyledon embryos. With culturing the mature somatic embryos on ½ basal medium containing 30 g/l of sucrose, 0.35% of phytagel and 2.5 mg/l–5.0 mg/l, preferably 5.0 mg/l, $GA_3$ together with Vc 100 mg/l, Asn 150 mg/l, CH 100 mg/l, Gln 150 mg/l, Pro 150 mg/l and 0.1% activated charcoal, 11% of mature somatic embryos germinated into seedlings. The seedlings were cultured on ½ basal medium containing 20 g/l of sucrose and 0.35% of phytagel and then transferred to pot soil consisting of peat soil: sand (3:1). The transplanted seedlings are then ready to be planted in the field.

Histological analysis showed that somatic embryogenesis was of unicellular origin from single epidermal cell of embryogenic callus. The somatic embryogenesis underwent 2-cell stage, proembryo stage; globular embryo stage, torpedo stage and cotyledon stage. Proembryonic structure was divided from maternal callus by one demarcation cell layer and globular embryo connected to callus by a suspensor-like structure.

Somatic embryogenesis has been used as the method of large-scale propagation of oil palm (Huong, 1999; Aberlenc-Bertossi et al., 1999) and soybean (Trick, 1997), and has been also used in other woody plants such as *Dalbergia sissoo* Roxb (Das et al., 1997), *Camellia sinensis* (L). O. Kuntze (Ponsamuel et al., 1996), and *Picea abies* (L.) Karst (Westcott, 1994). One of important applications of somatic embryogenesis is for genetic modification. For example, soybean somatic embryogenesis provided the main approach to breed high quality transgenic soybean plants (Trick, 1997). Combination of embryogenesis and Agrobacterium-mediated transformation had also succeeded in English walnut, pecan, and cherry, and will be very important in breeding (Kozlowski and Pallardy, 1997). *A. mangium* is a commercially important tropical legume tree for paper and pulp industry and a leading tree for plantation. Combination of an efficient regeneration system through somatic embryogenesis, as described herein, with biolistic or Agrobacterium-mediated transformation provides a valuable alternative for breeding pest or disease resistance.

EXAMPLES

The present invention is further detailed in the following Examples, which are offered by way of illustration and are not intended to limit the invention in any manner. Standard techniques well known in the art or the techniques specifically described below are utilized.

Example 1

Reagents and Culture Media

A. MS basic medium: MS medium (Murashige and Skoog, 1962)

| Name | Molecular formula | Concentration (mg/L) | Sigma Cat. No. |
|---|---|---|---|
| Macronutrients | | | |
| Ammonium Nitrate | $NH_4NO_3$ | 1,650 | A-3795 |
| Potassium Nitrate | $KNO_3$ | 1,900 | P-8291 |
| Calcium Chloride dihydrate | $CaCl_2.2H_2O$ | 440 | C-2536 |
| Magnesium Sulfate Heptahydrate | $MgSO_4.7H_2O$ | 370 | M-7774 |
| Potassium phosphate monobasic, anhydrous | $KH_2PO_4$ | 170 | P-8416 |
| Ferrous Sulfate Heptahydrate | $FeSO_4.7H_2O$ | 27.8 | F-8263 |
| Ethylenediamine-tetra-acetic acid (EDTA) | $C_{10}H_{14}N_2O_8Na_2.2H_2O$ ($Na_2EDTA$) | 37.3 | B-6635 |
| Micronutrients | | | |
| Potassium Iodide | KI | 0.83 | P-8166 |
| Boric Acid | $H_3BO_3$ | 6.2 | B-9645 |
| Manganese Sulfate monohydrate | $MnSO_4.H_2O$ | 6.9 | M-7899 |
| Zinc Sulfate | $ZnSO_4.7H_2O$ | 8.6 | Z-1001 |
| Molybdic Acid (Sodium salt:dihydrate) | $Na_2MoO_4.2H_2O$ | 0.25 | M-1651 |
| Cupric Sulfate (Pentahydrate) | $CUSO_4.5H_2O$ | 0.025 | C-3036 |
| Cobalt Chloride | $CoCl_2.6H_2O$ | 0.025 | C-2911 |
| Organic Reagents | | | |
| myo-Inositol | $C_6H_{12}O_6$ | 100 | I-3011 |
| Nicotinic acid | $C_6H_5NO_2$ | 0.5 | N-0765 |
| Glycine | $C_2H_5NO_2$ | 2.0 | G-6143 |
| Thiamine (Vitamin B1) | $C_{12}H_{17}ClN_4OS.HCl$ | 0.1 | T-3902 |
| Pyridoxine (Vitamin B6) Hydrochloride | $C_8H_{11}NO_3.HCl$ | 0.5 | P-9755 |

B. Other Organic Reagents

| Name | Molecular formula | Sigma Cat. No. |
|---|---|---|
| L-Ascorbic acid (Vitamin C) | $C_6H_8O_6$ | A-2174 |
| Casein Enzymatic Hydrolysate (CH) | | C-7290 |
| L-Glutamine (Gln) | $C_5H_{10}N_2O_3$ | G-9273 |
| L-Asparagine monohydrate (Asn) | $C_4H_8N_2O_3.H_2O$ | A-4284 |
| L-Proline (Pro) | $C_5H_9NO_2$ | P-4655 |
| Sucrose | | S-5390 |

-continued

C. Plant Growth Regulators

| Name | Sigma Cat. No. |
|---|---|
| 2,4-Dichlorophenoxyacetic Acid (2,4-D) | D-8407 |
| Indole-3-acetic Acid (IAA) | I-2886 |
| α-Naphthaleneacetic Acid(NAA) | N-0640 |
| 1-Phenyl-3-(1,2,3-thiadiazol-5-yl)Urea (Thidiazuron, TDZ) | P-6186 |
| 6-Benzylaminopurine (6-BA) | B-3408 |
| Kinetin (KT) | K-0753 |
| Gibberellic Acid (GA$_3$) | G-7645 |

D. Agar: Phytagel (Sigma catalog No.: P-8169)

E. Media for callus induction[1]

| AM-5 | MS + 2,4-D 2.0 mg/L + KT 3.0 mg/L |
|---|---|
| AM-6 | MS + 2,4-D 2.0 mg/L + KT 0.5 mg/L |
| AM-7 | MS + NAA 2.0 mg/L + KT 3.0 mg/L |
| AM-8 | MS + NAA 2.0 mg/L + KT 0.5 mg/L |
| AM-14 | MS + 2,4-D 0.5 mg/L + 6-BA 3.0 mg/L |
| AM-22 | MS + 2,4-D 2.0 mg/L + 6-BA 1.0 mg/L |
| AM-27 | MS + NAA 0.5 mg/L + 6-BA 3.0 mg/L |
| AM-31 | MS + NAA 0.5 mg/L + 6-BA 1.0 mg/L |
| AM-230 | MS + 2,4-D 5.0 mg/L + KT 3.0 mg/L |
| AM-231 | MS + 2,4-D 5.0 mg/L + KT 0.5 mg/L |
| AM-234 | MS + 2,4-D 1.0 mg/L + KT 1.0 mg/L |
| AM-265 | MS + IAA 0.25 mg/L + TDZ 1.0 mg/L |
| AM-304 | MS + IAA 0.25 mg/L + TDZ 2.0 mg/L |
| AM-308 | MS + IAA 2.0 mg/L + TDZ 1.0 mg/L |

[1]All media also contained CH 100 mg/L, Vc 100 mg/L, Gln 150 mg/L, Asn 150 mg/L and Pro 150 mg/L, phytagel 0.30%, sucrose 30 g/L, pH 5.8 after autoclaving.

F. Media for Embryo Maturation and Germination[1]

| AM-423 | ½MS + sucrose 30.0 mg/L |
|---|---|
| AM-424 | ½MS + GA$_3$ 5.0 mg/L + sucrose 30.0 mg/L |
| AM-425 | ½MS + sucrose 50.0 mg/L |
| AM-426 | ½MS + GA$_3$ 5.0 mg/L + sucrose 50.0 mg/L |
| AM-467 | ½MS + GA$_3$ 2.5 mg/L + sucrose 30.0 mg/L |

[1]All media also contained CH 100 mg/L, Vc 100 mg/L, Gln 150 mg/L, Asn 150 mg/L and Pro 150 mg/L, phytagel 0.30%, activated charcoal 0.1%, pH 5.8 after autoclaving G. Seedling Growth (Acclimatization)

½MS, sucrose 20.0 mg/L, 0.35% phytagel

H. Transplantation

Peat soil:white sand 3:1

Example 2

Plant Materials

One and half months old immature green pods were collected from twenty-meter high adult *A. mangium* Willd. trees at Science Park Drive of Singapore. Green seeds were gently isolated from pods and washed with sterile double deionized water (ddH$_2$O) 4–5 times. After green seeds were surface sterilised with 30% market clorox bleach (NaClO) for 5 minutes and washed with sterile ddH$_2$O 5 times, the seeds were sterilised again with 0.1% HgCl$_2$ for 6 minutes and washed with sterile ddH$_2$O 5 times. Seed coats were removed with sterilised forceps and embryos were isolated. Embryo axes (EA) (FIG. 1A) were gently separated with sterile forceps and used as explants for embryogenic callus induction.

Example 3

Culture Conditions

All media were adjusted to pH 5.8 after autoclaving at 121° C. for 25 min. Plant growth regulators tested in experiments were added into media after autoclaving but other additional substances were added into media before autoclaving. All cultures were maintained under the warm white fluorescent lights at a range of irradiance of 23.41–26.01 $\mu mol.s^{-1}m^{-2}$, with 16 h photoperiod and at 28° C.

Example 4

Histology

Embryogenic calli were fixed in 2.5% glutaraldehyde in 50 mM pH7.2 sodium phosphate buffer at room temperature overnight, then dehydrated through a graded ethanol series 20%, 30%, 50%, 70%, and 90% sequentially for 20 minutes thrice, at last in 100% ethanol for 30 minutes thrice. All tissues were embedded in plastics (Leica plastic embed Kit) and were sectioned at a thickness of 5–10 $\mu m$. All sections were stained in 0.025% toluidine blue for 1 minute, dried at 42° C., mounted with DPX (BDH), and examined under a light microscope (Leica).

Example 5

Scanning Electron Microscopy

Embryogenic calli were treated with liquid nitrogen, and examined by scanning electron microscopy (JSM-5310LV, JEOL Company, Japan).

Example 6

Embryogenic Callus Induction

EAs were cultured for two months on MS basal medium (Murashige and Skoog 1962) supplemented with different combinations of plant growth regulators: 2,4-D (1.0–5.0 mg/l) and KT (0.5–3.0 mg/l), 2,4-D (0.5–2.0 mg/l) and 6-BA (1.0–3.0 mg/l), NAA (0.5 mg/l) and 6-BA (1.0–3.0 mg/l), NAA (0.5–2.0 mg/l) and KT (0.5–3.0 mg/l) or IAA (0.25–2.0 mg/l) and TDZ (1.0–2.0 mg/l). Each experiment was repeated twice. A total of 90 embryo axes were tested for embryogenic callus induction on each plant growth regulator combination. All media contained ascorbic acid (Vc) 100 mg/l, asparagine (Asn) 150 mg/l, casein enzymatic hydrolysate (CH) 100 mg/l, glutamine (Gln) 150 mg/l, and proline (Pro) 150 mg/l, sucrose 30 g/l and phytagel 0.3% (g/l) in this experiment.

Figures 1A, 1B, 1C, 1D:
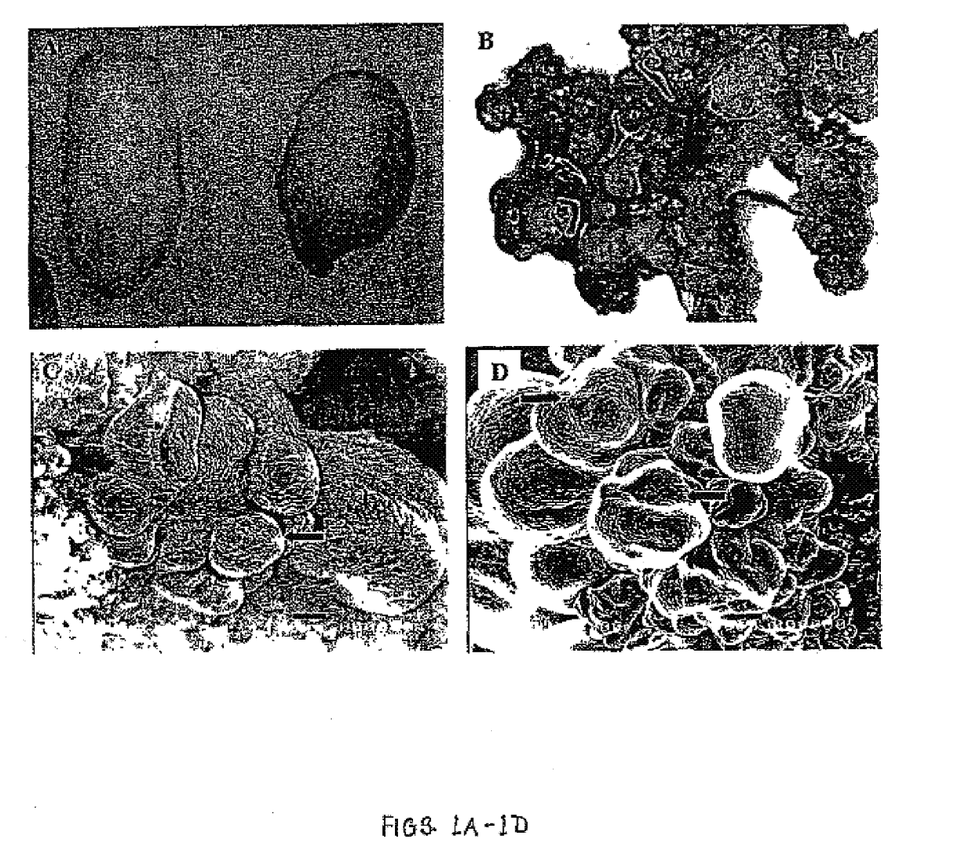
FIG. 1A shows the use of the embryo axis as the explant to induce embryogenic callus.
FIG. 1B shows embryogenic callus induced on the induction medium AM-304.
FIGS. 1C–D show scanning electron microscopy of *Acacia maligium* somatic embryos with FIG. 1C showing globular stages (indicated by arrow; bar=100 μm) and FIG. 1D showing heart stage (indicated by arrow; bar=100 μm).

It was reported that the initiation of somatic embryo production from callus occurs in the media containing high concentrations of auxin or a high ratio of auxin to cytokinin (Kozlowski and Pallardy, 1997). However, in *A. mangium* somatic embryogenesis, green-yellowish and friable embryogenic calli were obtained only on the media containing the combinations of 1.0–2.0 mg/l TDZ and 0.25–2.0 mg/l IAA, (Table 1; FIG. 1B). The combination of TDZ 2.0 mg/l and IAA 0.25 mg/l was the most efficient for induction of embryogenic calli (16.41%) (Table 1), which then produced globular embryos and heart embryos (FIGS. 1B–D). This combination was used to induce more embrygenic calli. However, on the media containing 2,4-D (1.0–5.0 mg/l) and KT (0.5–3.0 mg/l), 2,4-D (0.5–2.0 mg/l) and 6-BA (1.0–3.0 mg/l), NAA (0.5 mg/l) and 6-BA (1.0–3.0 mg/l) or NAA (0.5–2.0 mg/l) and KT (0.5–3.0 mg/l), no embryogenic callus was obtained (Table 1). Rout et al. (1995) reported that the combination of kinetin 13.9 μM (2.99 mg/l) and NAA 2.7 μM (0.55 mg/l) promoted *A. catechu* somatic embryogenesis from immature cotyledon. However, the similar combination of NAA and KT did not induce any embryogenic callus from *A. mangium* immature embryonic axis (Table 1). The callus induced from embryonic axis was white and loose on the medium containing NAA and KT. The Acacia genus comprises more than 1,200 species and big variations in morphology (Simmons, 1987) were documented. Among other differences, an adult *A. mangium* is about 30 meters tall while one adult *A. catechu* is only 9–12 meters. The variation of responses to plant growth regulators may result from the differences of genetic background among species. TDZ was recommended in woody species tissue culture especially in recalcitrant species (Lu, 1993). Our results showed that TDZ was effective to induce embryogenic callus in *A. mangium*. Chengalrayan et al. (1997) reported that the substitution of 6-BA and KT with TDZ increased peanut plant recovery through somatic embryogenesis.

TABLE 1

The Effects of the Different Combinations of Plant Growth Regulators on Embryogenic Callus Induction

| Medium No. | 2,4-D (mg/l) | NAA (mg/l) | IAA (mg/l) | TDZ (mg/l) | 6-BA (mg/l) | KT (mg/l) | Frequency of explants forming embryogenic callus[1] |
|---|---|---|---|---|---|---|---|
| AM-234 | 1.0 |  |  |  |  | 1.0 | 0 |
| AM-6 | 2.0 |  |  |  |  | 0.5 | 0 |
| AM-5 | 2.0 |  |  |  |  | 3.0 | 0 |
| AM-231 | 5.0 |  |  |  |  | 0.5 | 0 |
| AM-230 | 5.0 |  |  |  |  | 3.0 | 0 |
| AM-14 | 0.5 |  |  |  | 3.0 |  | 0 |
| AM-22 | 2.0 |  |  |  | 1.0 |  | 0 |
| AM-31 |  | 0.5 |  |  | 1.0 |  | 0 |
| AM-27 |  | 0.5 |  |  | 3.0 |  | 0 |
| AM-23 |  | 0.5 |  |  |  | 3.0 | 0 |
| AM-7 |  | 2.0 |  |  |  | 3.0 | 0 |
| AM-8 |  | 2.0 |  |  |  | 0.5 | 0 |
| AM-265 |  |  | 0.25 | 1.0 |  |  | 11.06 ± 0.94 |
| AM-304 |  |  | 0.25 | 2.0 |  |  | 16.41 ± 4.75 |
| AM-308 |  |  | 2.0 | 1.0 |  |  | 3.51 ± 3.35 |

[1]% (mean ± SD); data correspond to average results of three replicates.

Figure 3A:
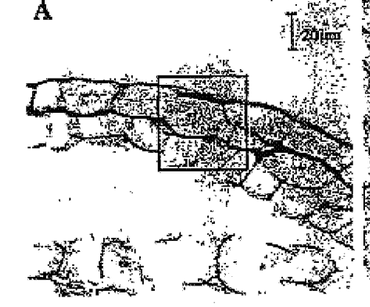
FIGS. 3A–D show somatic embryo initiation from epidermis cell as follows: metaphase (A and B, indicated by arrow), two-daughter cells (C, indicated by arrow), and proembryonic structure (D)
Figure 3B:
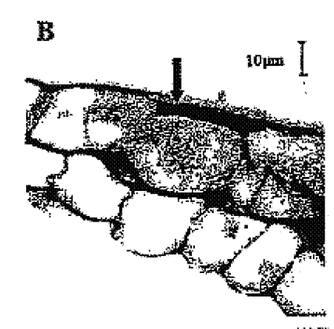
Figure 3C:
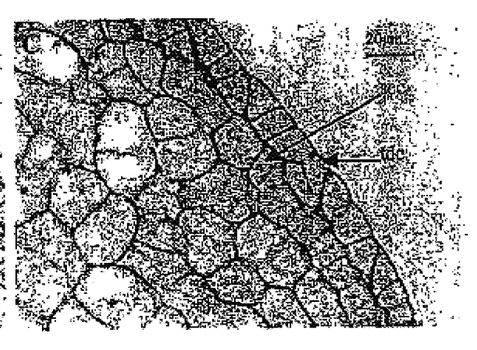
Figure 3D:
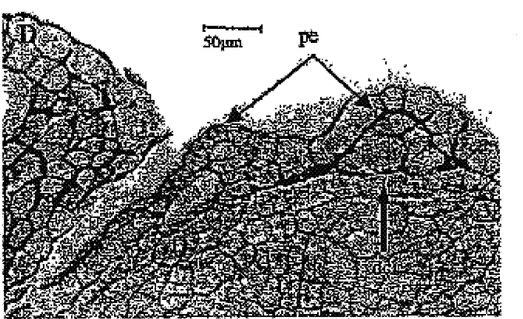
Figure 3E:
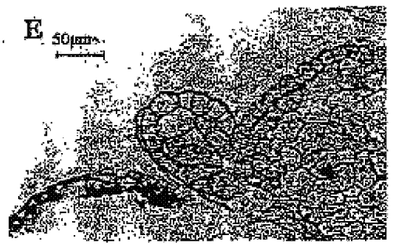
Figure 3F:
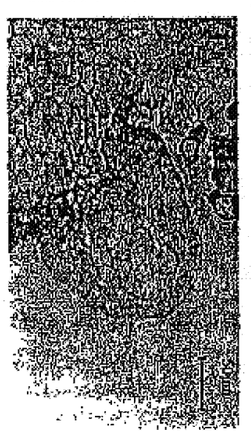
Figures 3G, 3H:
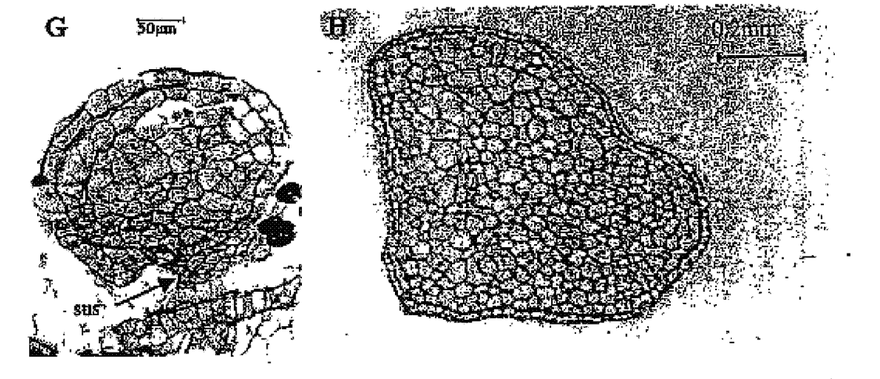

The combination of TDZ (2.0 mg/l) and IAA (0.25 mg/l) promoted somatic embryogenesis of *A. mangium*. However, somatic embryo development stopped at the heart stage (FIG. 1D; FIG. 3H) and secondary somatic embryos formed if heart embryos were kept longer on the same induction medium. Somatic embryos could not develop forward to later stages. Thus, it was necessary to mature the somatic embryos.

Example 7

Somatic Embryo Maturation and Germination

Globular embryos (FIGS. 1B–C) induced from induction medium containing IAA 0.25 mg/l and TDZ 2.0 mg/l (AM-304) were cultured on ½ MS basal medium supplemented with 0–5.0 mg/l of $GA_3$, 30–50 g/l of sucrose, Vc 100 mg/l, Asn 150 mg/l, CH 100 mg/l, Gln 150 mg/l, Pro 150 mg/l, phytagel 0.35% (g/l), and activated charcoal 0.1% for thirty days. Somatic embryos were then transferred onto maturation medium AM-425 and cultured for 40 days. Cotyledon somatic embryos (mature somatic embryos) were then transferred onto the medium AM-424 for germination. Each experiment was repeated twice with a total of 250 globular somatic embryos for each medium combination. Seedlings were transferred to ½ MS basal medium containing sucrose 20 g/l as well as phytagel 0.35% and cultured for two months before being transferred to pot soil consisting of peat soil: sand (3:1).

The maturation of the somatic embryos was in agreement with the results from others that maturation was very important in plant regeneration via somatic embryogenesis (Kozlowski and Pallardy, 1997; Huong 1999). Two steps of maturation procedure were used for somatic embryo maturation. Firstly, somatic embryos were treated in medium containing 0.35% of phytagel and 2.5–5.0 mg/l of $GA_3$ (maturation medium AM-424, AM-426, and AM-467) (Table 2). Secondly, somatic embryos were transferred onto media containing 50 g/l of sucrose and 0.35% of phytagel (maturation medium AM-425) for desiccation. The treatment on medium AM-424 followed by AM-425 promoted 42.33% globular somatic embryos to develop into torpedo and cotyledon embryos (FIG. 2A; Table 2).

TABLE 2 the Effects of Different Media on Somatic Embryo Maturation

| Media No. | Basal medium | GA3 (mg/l) | Sucrose (g/l) | Frequency of globular embryos producing torpedo and cotyledon somatic embryos[1] |
|---|---|---|---|---|
| AM-424 | ½MS | 5.0 | 30 | 42.33 ± 13.65 |
| AM-467 | ½MS | 2.5 | 30 | 18.67 ± 6.11 |
| AM-426 | ½MS | 5.0 | 50 | 26.67 ± 8.33 |
| AM-423 | ½MS | 0 | 30 | 0 |
| AM-425 | ½MS | 0 | 50 | 0 |

[1]% (mean ± SD); data correspond to average results of three replicates.

Further development of globular somatic embryos to torpedo stage and cotyledon stage was not observed on the maturation media without $GA_3$ (AM-423 and AM425) (Table 2). These results indicated that $GA_3$ promoted somatic embryo maturation. Our results were opposite to the reports that the presence of GAs during both the induction and expression phases of geranium (*Pelargonium x hortorum* Bailey) somatic embryogenesis was detrimental to somatic embryo formation on the hypocotyl explants (Hutchinson et al.,1997). In our experiment, somatic embryo maturation was completed on a relatively high sucrose concentration. The similar results were reported in Populus somatic embryo embryogenesis that sucrose concentrations between 20–50 g/l stimulated somatic embryo differentiation (Michler and Bauer 1991). Biahoua and Bonnean (1999) reported that a high sucrose concentration of 350 mM (120 g/l) gave the most efficiency of *Euonymus europaeus* somatic embryogenesis and suggested two roles of the high sucrose concentration in somatic embryogenesis including one nutritious factor and the other osmotic potential in culture medium. Maturation of somatic embryogenesis was critical for many plants such as soybean somatic embryogenesis (Ranch et al.1986) and *Picea abies* (Jalonen and Arnold 1991). Adding 6% of maltose in medium promoted soybean somatic embryo histodifferentiation and maturation (Ranch et al.1986). For *Picea abies* somatic embryo maturation, ABA treatment was necessary in medium (Jalonen and Arnold 1991). In our experiment, abnormal cotyledon embryos, such as somatic embryos with only one cotyledon (FIG. 2F) or with three cotyledon structures, which could not germinate into seedling, were also observed.

Example 8

Histology of the Somatic Embryogenesis

Figures 2A, 2B, 2C, 2D, 2E, 2F:
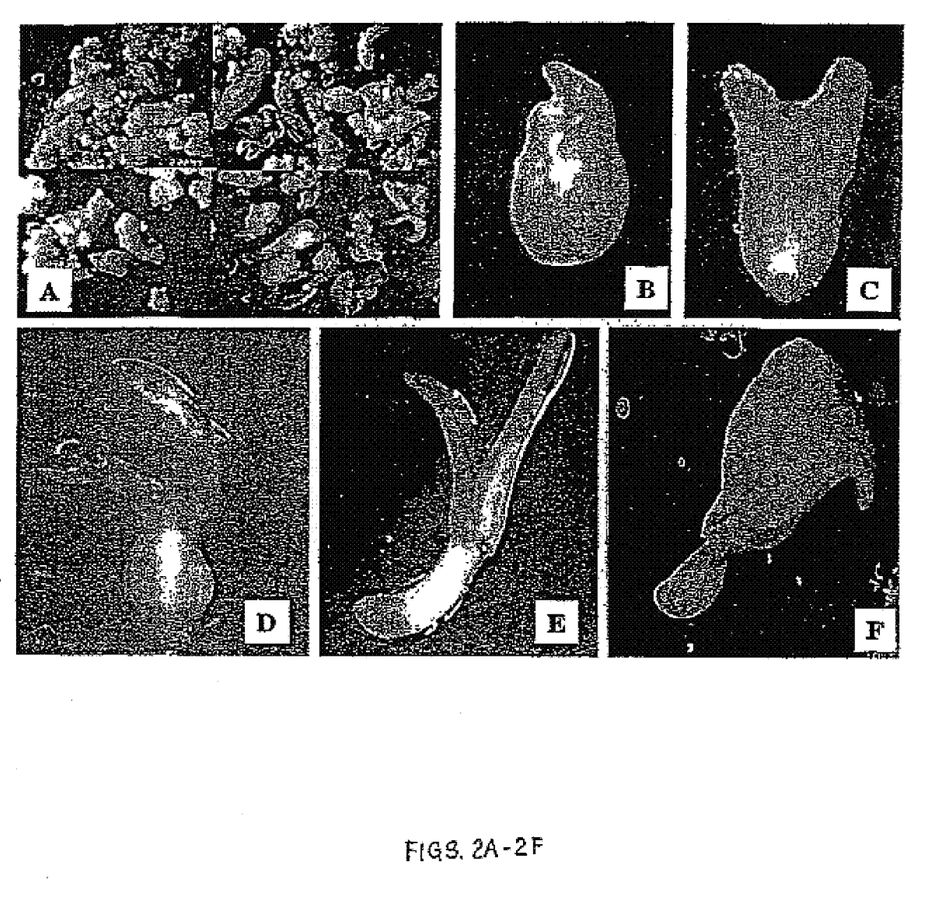

Somatic embryogenesis has been considered a model for the understanding of plant embryo development (Warren, 1993). Two distinct types of somatic embryogenesis have been recognized. One is direct embryogenesis, in which one single cell (or cell group) commences meristematic growth and all the descendants of this cell form part of embryo (Warren, 1993). The other is indirect embryogenesis, in which an embryo develops from one cell in a previously formed meristematic cluster (Warren, 1993). In *A. mangium*, the embryogenesis belongs to indirect somatic embryogenesis. Histological sections showed that somatic embryogenesis developed from one epidermal cell of embryogenic callus (FIGS. 3A–D). Periclinal division of the cell produced 2-daughter cells (FIGS. 3A–C), one outer daughter cell and one inner daughter cell (FIG. 3C). The continuous cell division of two daughter cells formed proembryonic structure (FIG. 3D) which developed further into globular embryo and heart embryo (FIGS. 3E–H). In the light of histological analysis, it is believed that the outer daughter cell developed into epidermal cells of somatic embryo but the inner daughter cell developed into somatic embryo body. Histological sections also showed that sub-epidermal cells next to epidermal cell did not form somatic embryo but their anticlinal division formed a demarcation layer cells to divide somatic embryo and maternal callus (FIGS. 3C–G). This structure of the layer cells between proembryonic structure and maternal callus to demarcate somatic embryo and maternal callus was called demarcation cell layer in this paper (FIG. 3D). From proembryonic structure to globular embryo, one suspensor-like structure formed at the base of globular embryo (FIG. 3G). On the induction medium, embryo development stopped at heart embryo stage (FIG. 1D; FIG. 3H). Through maturation, globular embryos developed forward to torpedo embryos (FIG. 2B) and cotyledon embryos (FIGS. 2C–D). In conclusion, somatic embryogenesis underwent two-cell stage (FIG. 3C), proembryo stage (FIG. 3D), globular stage (FIGS. 3E–G), heart stage (FIG. 1D; FIG. 3H), torpedo stage (FIG. 2B), and cotyledon stage (FIGS. 2C–D).

Example 9

Somatic Embryo Germination

Figure 4A:
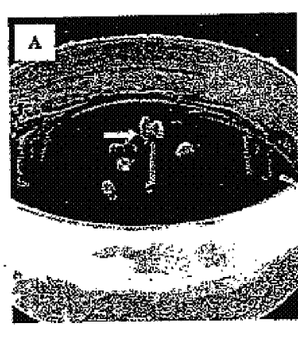
FIG. 4A shows germinating mature somatic embryo with the pinnate leaf (indicated by arrow), elongated hypocotyl and radicle in medium.
Figure 4B:
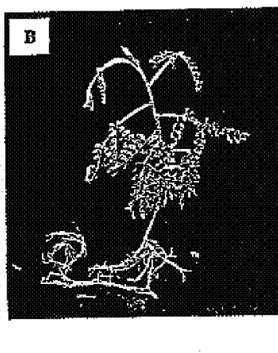
FIG. 4B shows seedling before planting into soil.
Figure 4C:
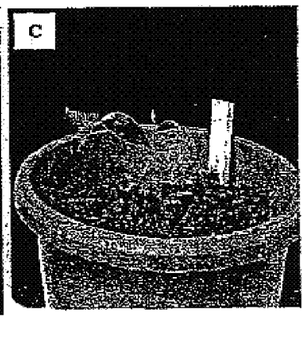
FIG. 4C shows plant growing in soil (3:1).

Normal somatic embryo germination included radicle elongation, hypocotyl elongation and the first pinnate leaf expansion. Only those mature somatic embryos consisting of radicle, hypocotyl, cotyledon and the first pinnate leaf structure could germinate into free-living seedlings (FIGS. 4B–C). On the medium AM-424 containing $GA_3$ 5.0 mg/l, 11% of somatic embryos germinated to seedlings with root, the first pinnate leaf (FIG. 4A, arrow), and elongated hypocotyl. Somatic embryos with radicle and hypocotyl elongation but without the first pinnate leaf formation could not germinate to seedlings. Somatic embryos with the first pinnate leaf formation but without radicle elongation could be rescued by rooting or micropropagation. Abnormal embryos like those somatic embryos with big single cotyledon (FIG. 2F) or three cotyledon structures could not germinate into seedlings.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

List of References

Aberlenc-Bertossi, F. et al. (1999). *Plant, Cell, Tiss. And Org. Cult* 56:53–57.

Ahmad, D. H. (1991). *Journal of Tropical Forest Science* 3:204–208.
Bajaj, Y. P S. (1995). "Somatic embryogenesis and its applications for crop improvement." Chapter II1.1. In: Biotechnology in Agriculture and Forestry. 30. Somatic Embryogenesis and Synthetic Seed. I. (Ed: Y. P S. Bajaj). Springer-Verlag:105–125.
Bayliss, M. (1998a). *Asia Pacific Papermaker* 8: 19
Bayliss, M. (1998b). *Asia Pacific Papermaker* 8: 64
Bhaskan, P. and Subbash, K. (1996). *Indian Journal of Experimental Biology* 34:590–591.
Biahoua, A. and Bonnean L. (1999). *Plant Cell Rep.* 19:185–190.
Chengalrayan, K. et al. (1997). *Plant Cell Rep.* 16:783–786,
Das, P. et al. (1997). *Plant Cell Rep.* 16:578–582.
Galiana, A. et al. (1991a). *Plant and Soil* 135:151–159.
Galiana, A. et al (1991b). *Plant and Soil* 35:161–166.
Huong, L. T. L. et al. (1999). *Plant Cell Rep.* 56:1–7.
Hutchinson, M. J. (1997). *Plant Cell Rep.* 16:435–438.
Jalonen, P. and Arnold, S. V. (1991). *Plant Cell Rep.* 10:384–387.
Kozlowski, T. T. and Pallardy, S. G. (1997). "Biotechnology." In: *Growth Control in Woody Plants*, Kozlowski T T, Pallardy S G (eds), Academic Press, New York, pp436–479.
Lu, C. Y. (1993). *In Vitro Cell Dev. Biol.* 29P:92–96
Mathews, H. et al. (1992). *In Vitro Cell Dev. Biol.* 28:172–178.
Michler, C. H. and Bauer, E. O. (1991). *Plant Sci* 77:111–177.
Murashige, T. and Skoog, F. (1962). *Physiol. Plant* 15:473–497.
Neuhaus, G. G. et al. (1987). *Theor. Appl. Genet.* 75:30–36.
Ponsamuel, J. et al. (1996). *Plant Cell Rep.* 16:210–214.
Ranch, J. P. et al. (1986). "Plant regeneration from tissue cultures of soybean by somatic embryogenesis." In: *Cell Culture and Somatic Cell Genetics of Plants*, Vasil I K (eds), Academic Press, New York, pp. 97–110.
Rao, G. V. R. and Prasad, M. N. V. (1991). *J. Plant Physiol.* 137: 625–627.
Robinson, C. (1999). *Nature Biotechnology* 17: 27–30.
Rout, G. R. et al. (1995). *Plant Cell. Tiss. and Org. Cult.* 42:283–285
Sedgley, M. et al. (1992). *Austrialian Journal of Botany* 1:37–48.
Simmons, M. H. (1987). *Acacias of Australia*, Vol.1, Nelson Publishers, pp1–31.
Sornsathapornkul, P. and Owens, N. J. (1999). *J. Plant Sci.* 160:229–240.
Toshihiro, O. and Sonoko, T. (1999). *J. Plant Physiology* 155:110–113.
Trick, H. N. et al. (1997). *Plant Tiss. Cult. Biotechnol.* 3:9–26.
Tsai, L. M. (1988). *Journal of Tropical Ecology* 4:293–302.
Tzfira, T. et al. (1998). *TIBTECH* 16:439–446.
Warren, G. (1993). "The regeneration of plants from cultured cells and tissues." In: *Plant Cell and Tissue Culture*, Stafford A, Warren G (eds), John Wiley & Sons, Chichester, England, pp. 82–100
Westcott, R. J. (1994). *Plant Cell Rep.* 14:47–49.
Wilde, H. D. et al. (1992). *Physiol.* 98:114–120.

What is claimed is:

1. A method for preparing somatic embryos of *Acacia mangium* comprising:
 a) culturing an explant on callus induction medium to induce embryogenic callus and globular embryo formation; and
 b) culturing globular embryos on a maturation medium to form somatic embryos.

2. The method of claim 1, wherein said step (b) comprises:
 b1) culturing globular embryos on a first maturation medium and
 b2) culturing the embryos on a second maturation medium.

3. A method for regenerating *Acacia mangium* comprising:
 a) culturing an explant on callus induction medium to induce embryogenic callus and globular embryo formation;
 b) culturing the globular embryos on a maturation medium to form somatic embryos; and
 c) culturing the somatic embryos on a germination medium to produce regenerated seedlings.

4. The method of claim 3, wherein said step (b) comprises:
 b1) culturing globular embryos on a first maturation medium and
 b2) culturing the embryos on a second maturation medium.

5. The method of claim 3, wherein the regenerated seedlings are cultured on an acclimatizing medium.

6. The method of claim 4, wherein the regenerated seedlings are cultured on an acclimatizing medium.

7. The method of claim 1, wherein the explant is an immature embryo.

8. The method of claim 7, wherein the callus induction medium comprises MS basal medium supplemented with a) thidiazuron, b) indole-3-acetic acid, c) casein enzymatic hydrolysate, d) L-ascorbic acid, e) L-glutamine, f) L-asparagine, g) L-proline, h) sucrose and i) phytagel.

9. The method of claim 8, wherein the callus induction medium comprises 1.0 mg/l to 2.0 mg/l thidiazuron and 0.25 mg/l to 2.0 mg/l indole-3-acetic acid.

10. The method of claim 8, wherein the first maturation medium comprises ½ MS basal medium supplemented with a) gibberellic acid, b) casein enzymatic hydrolysate, c) L-ascorbic acid, d) L-glutamine, e) L-asparagine, f) L-proline, g) sucrose, h) activated charcoal and i) phytagel.

11. The method of claim 10, wherein the first maturation medium comprises 2.5 mg/l to 5.0 mg/l gibberellic acid and 30 g/l to 50 g/l sucrose.

12. The method of claim 8, wherein the second maturation medium comprises ½ MS basal medium supplemented with a) casein enzymatic hydrolysate, b) L-ascorbic acid, c) L-glutamine, d) L-asparagine, e) L-proline, f) sucrose, g) activated charcoal and h) phytagel.

13. The method of claim 10, wherein the second maturation medium comprises ½ MS basal medium supplemented with a) casein enzymatic hydrolysate, b) L-ascorbic acid, c) L-glutamine, d) L-asparagine, e) L-proline, f) sucrose, g) activated charcoal and h) phytagel.

14. The method of claim 8, wherein the germination medium comprises ½ MS basal medium supplemented with a) gibberellic acid, b) casein enzymatic hydrolysate, c) L-ascorbic acid, d) L-glutamine, e) L-asparagine, f) L-proline, g) sucrose, h) activated charcoal and i) phytagel.

15. The method of claim 14, wherein the germination medium comprises 2.5 mg/l to 5.0 mg/l gibberellic acid.

16. The method of claim 10, wherein the germination medium comprises ½ MS basal medium supplemented with a) gibberellic acid, b) casein enzymatic hydrolysate, c) L-ascorbic acid, d) L-glutamine, e) L-asparagine, f) L-proline, g) sucrose, h) activated charcoal and i) phytagel.

17. The method of claim 16, wherein the germination medium comprises 2.5 mg/l to 5.0 mg/l gibberellic acid.

18. The method of claim 13, wherein the germination medium comprises ½ MS basal medium supplemented with a) gibberellic acid, b) casein enzymatic hydrolysate, c) L-ascorbic acid, d) L-glutamine, e) L-asparagine, f) L-proline, g) sucrose, h) activated charcoal and i) phytagel.

19. The method of claim 18, wherein the germination medium comprises 2.5 mg/l to 5.0 mg/l gibberellic acid.

20. The method of claim 8, wherein the acclimatizing medium comprises ½ MS basal medium supplemented a) sucrose and b) phytagel.

21. The method of claim 18, wherein the acclimatizing medium comprises ½ MS basal medium supplemented a) sucrose and b) phytagel.

* * * * *